(12) United States Patent
Nicolas et al.

(10) Patent No.: US 8,604,241 B2
(45) Date of Patent: Dec. 10, 2013

(54) METHOD FOR SYNTHESIS OF (1S, 2R)-MILNACIPRAN

(75) Inventors: Marc Nicolas, Gaillac (FR); Paul Hellier, Castelnau de Montmiral (FR); Catherine Diard, Albi (FR); Laurent Subra, Montgaillard (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 217 days.

(21) Appl. No.: 13/146,361

(22) PCT Filed: Jan. 29, 2010

(86) PCT No.: PCT/EP2010/051045
§ 371 (c)(1),
(2), (4) Date: Jul. 26, 2011

(87) PCT Pub. No.: WO2010/086394
PCT Pub. Date: Aug. 5, 2010

(65) Prior Publication Data
US 2011/0295036 A1    Dec. 1, 2011

(30) Foreign Application Priority Data

Jan. 29, 2009   (FR) ..................... 09 50552

(51) Int. Cl.
*C07C 233/57*   (2006.01)
*C07C 231/06*   (2006.01)

(52) U.S. Cl.
USPC ............ 564/164; 564/124; 564/126; 564/190

(58) Field of Classification Search
USPC ................... 564/124, 126, 164, 190
See application file for complete search history.

(56) References Cited

U.S. PATENT DOCUMENTS

| 4,478,836 A | 10/1984 | Mouzin et al. |
| 5,034,541 A * | 7/1991 | Bigg et al. ............... 548/473 |
| 2008/0051604 A1* | 2/2008 | Niimoto et al. ............ 564/164 |

FOREIGN PATENT DOCUMENTS

| EP | 2 508 035 A1 | 12/1982 |
| EP | 0 200 638 A1 | 11/1986 |
| EP | 0 377 381 A1 | 7/1990 |
| EP | 0 747 348 A1 | 12/1996 |
| EP | 1 757 597 A1 | 2/2007 |
| EP | 1 767 522 A1 | 3/2007 |
| EP | 1 770 084 A1 | 4/2007 |
| EP | 1 845 084 A1 | 10/2007 |
| JP | 2007023005 | * 2/2007 |
| WO | WO 2005/118564 A2 | 12/2005 |

OTHER PUBLICATIONS

Bonnaud et al., Journal of Chromatography, 318, 1985, pp. 398-403.
Doyle et al., Adv. Synth. Catal. 2001, 343, pp. 299-302.
Roggen et al., Bioorganic Medicinal Chemistry Letters 2007, 17, pp. 2834-237.
Shuto et al., J. Med. Chem. 1995, 38, pp. 2964-2968.
Shuto et al., J. Org. Chem. 1996, 61, No. 3, pp. 915-923.
Shuto et al., Tetrahedron Letters, vol. 37, No. 5, 1996, pp. 641-644.
Tamiya et al., Bioorganic & Medicinal Chemistry Letters, 18, 2008, pp. 3328-3332.
Viazzo et al., Tetrahedron Letters, vol. 37, No. 26, 1996, pp. 4519-4522.
Wang et al., Chinese Journal of Pharmaceuticals 2004, 35, pp. 259-260.
Xu et al., Organic Letters, 2006, vol. 8, No. 17, pp. 3885-3888.

* cited by examiner

*Primary Examiner* — Shailendra Kumar
(74) *Attorney, Agent, or Firm* — Birch, Stewart, Kolasch & Birch, LLP

(57) ABSTRACT

The present invention relates to a method for synthesizing a pharmaceutically acceptable acid addition salt of (1S, 2R)-milnacipran comprising the following successive steps: (a) reaction of phenylacetonitrile and of (R)-epichlorhydrin in the presence of a base containing an alkaline metal, followed by a basic treatment, and then by an acid treatment in order to obtain a lactone; (b) reaction of said lactone with MNEt$_2$, wherein M represents an alkaline metal, or with NHEt$_2$ in the presence of a Lewis acid-amine complex, in order to obtain an amide-alcohol; (c) reaction of said amide-alcohol with thionyl chloride in order to obtain a chlorinated amide; (d) reaction of said chlorinated amide with a phthalimide salt in order to obtain a phthalimide derivative; (e) hydrolysis of the phthalimide group of said phthalimide derivative in order to obtain (1S, 2R)-milnacipran, and (f) salification of (1S, 2R)-milnacipran in a suitable solvent system in the presence of a pharmaceutically acceptable acid.

12 Claims, No Drawings

METHOD FOR SYNTHESIS OF (1S, 2R)-MILNACIPRAN

This application is a 371 of PCT/EP2010/051045, filed Jan. 29,2010.

The present invention relates to a method for asymmetric synthesis of (1S,2R)-milnacipran as well as to a chlorinated intermediate in the major (1S,2R) enantiomeric form.

Milnacipran is an antidepressant inhibiting recapture of serotonin-noradrenaline recommended in the treatment of depression (FR 2 508 035).

Many syntheses of the racemic compound have been described in the literature (EP 0 377 381; EP 0 200 638; EP 1 757 597; EP 1 767 522; EP 1 845 084; EP 1 770 084; Shuto S. et al., *J. Med. Chem.* 1995, 38, 2964-2968).

Moreover, it was recently demonstrated that the enantiomer (1S,2R)-milnacipran is more active than the racemic mixture (Viazzo P. et al., *Tetrahedron Lett.* 1996, 37, 26, 4519-4522).

A first method for obtaining this enantiomer in enriched form has been the separation or resolution of enantiomers from the racemic mixture (Bonnaud B. et al., *J. Chromatogr.* 1985, 318, 398-403). However, such a method is not cost-effective industrially since there is a loss of at least half of the product. Enantio-selective syntheses were then developed for preparing enantiomerically enriched milnacipran (Doyle M. P. and Hu W. *Adv. Synth. Catal.* 2001, 343, 299-302; Roggen H. et al., *Bioorg. Med. Chem.* 2007, 17, 2834-2837; Shuto S. et al., *Tetrahedron Lett.* 1996, 37, 641-644; Wang X.-Q. et al., *Chinese journal of Pharmaceuticals* 2004, 35, 259-260; WO 2005/118 564). However, most of these syntheses use sodium azide as a reagent, which may hardly be contemplated industrially because of its toxicity and of its instability which may lead to an explosion. Therefore there is still a significant need for new methods for synthesizing (1S,2R)-milnacipran which are more secure, more economical and more efficient.

Thus more particularly the object of the present invention is a method for the synthesis of a pharmaceutically acceptable acid addition salt of (1S,2R)-milnacipran of the following formula (I):

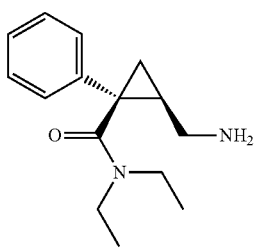

(I)

comprising the following successive steps:
(a) reaction of phenylacetonitrile and of (R)-epichlorhydrin in the presence of a base containing an alkaline metal, followed by a basic treatment, and then by an acid treatment in order to obtain the lactone of the following formula (II):

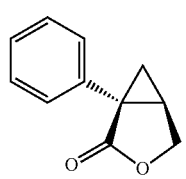

(II)

(b) reaction of the lactone (II) obtained in the previous step (a) with MNEt$_2$, wherein M represents an alkaline metal, or with NHEt$_2$ in the presence of a Lewis acid-amine complex wherein the amine is selected from diethylamine, triethylamine, diisopropylethylamine, N,N-diethylaniline, N,N-dimethylbenzylamine, N-methylpiperidine, N-methylmorpholine, N,N'-dimethylpiperazine and hexamethylene tetramine, in order to obtain the amide-alcohol of the following formula (III):

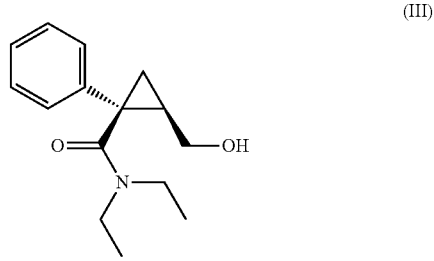 [SMILES: CCN(CC)C(=O)[C@@]1(c2ccccc2)C[C@H]1CO]

(III)

(c) reaction of the amide-alcohol of formula (III) obtained in the previous step (b) with thionyl chloride in order to obtain the chlorinated amide of the following formula (IV):

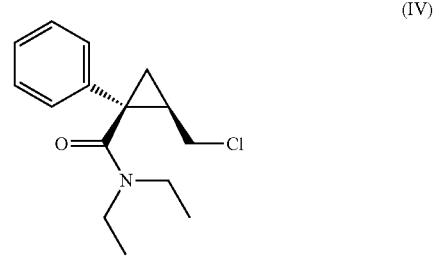 [SMILES: CCN(CC)C(=O)[C@@]1(c2ccccc2)C[C@H]1CCl]

(IV)

(d) reaction of the chlorinated amide of formula (IV) obtained in the previous step (c) with a phthalimide salt, such as the potassium salt, in order to obtain the phthalimide derivative of the following formula (V):

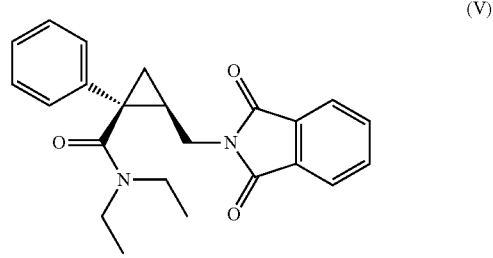 [SMILES: CCN(CC)C(=O)[C@@]1(c2ccccc2)C[C@H]1CN1C(=O)c2ccccc2C1=O]

(V)

(e) hydrolysis of the phthalimide group of the phthalimide derivative of formula (V) obtained in the previous step (d) in order to obtain (1S, 2R)-milnacipran, and
(f) salification of (1S,2R)-milnacipran obtained in the previous step (e) in a suitable system of solvents, in the presence of a pharmaceutically acceptable acid.

In the present invention, <<pharmaceutically acceptable>> describes what is useful in the preparation of a pharmaceutical composition which is generally safe, non-toxic and neither biologically nor otherwise undesirable, and which is acceptable for veterinary use as well as for human pharmaceutical use.

A <<pharmaceutically acceptable acid addition salt>> of a compound is meant to designate in the present invention, salts which are pharmaceutically acceptable, as defined here, which have the desired pharmacological activity of the parent compound and which are obtained by addition of a pharmaceutically acceptable acid on the compound.

By <<pharmaceutically acceptable acid>> is notably meant inorganic acids such as hydrochloric acid, hydrobromic acid, sulfuric acid, nitric acid, phosphoric acid, and the like, or organic acids such as acetic acid, benzene-sulfonic acid, benzoic acid, camphor-sulfonic acid, citric acid, ethane-sulfonic acid, fumaric acid, glucoheptonic acid, gluconic acid, glutamic acid, glycolic acid, hydroxynaphthoic acid, 2-hydroxyethane-sulfonic acid, lactic acid, maleic acid, malic acid, mandelic acid, methane-sulfonic acid, muconic acid, 2-naphthalene-sulfonic acid, propionic acid, salicylic acid, succinic acid, dibenzoyl-L-tartaric acid, tartaric acid, p-toluene-sulfonic acid, trimethylacetic acid, trifluoroacetic acid, and the like. Preferably, this is hydrochloric acid.

Step (a):

This step corresponds to the following reaction sequence:

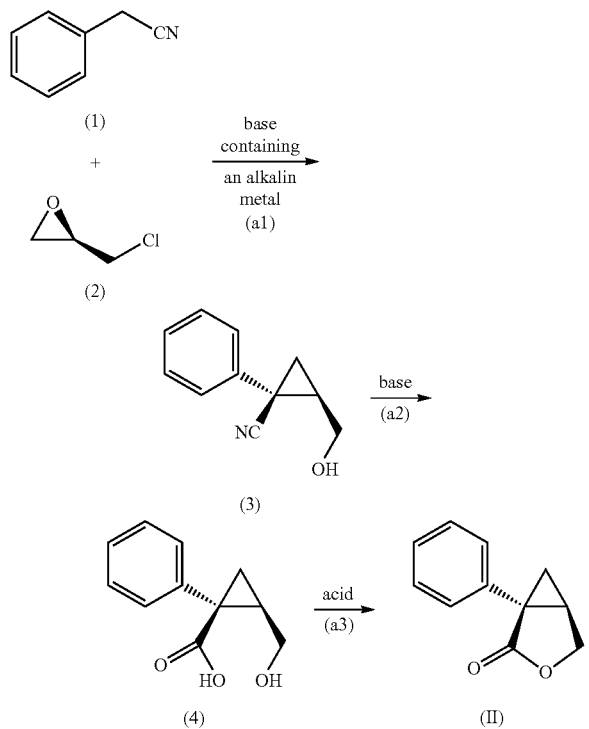

By <<base containing an alkaline metal>> is meant in the sense of the present invention, a base of formula RM, wherein:

M represents an alkaline metal, and in particular sodium (Na), potassium (K) or lithium (Li), and R represents a hydrogen atom, an alkyl (such as butyl or hexyl), alkoxy (such as tertiobutyloxy) or $NR^1_2$ group, with $R^1$ representing a hydrogen atom, an alkyl (such as isopropyl) or $Si(CH_3)_3$ group.

By <<alkyl>> is meant in the sense of the present invention, a saturated, linear or branched hydrocarbon chain, comprising from 1 to 6 carbon atoms. In particular this will be a butyl, hexyl or isopropyl group.

By <<alkoxy>> is meant in the sense of the present invention, an alkyl group as defined above, bound to the remainder of the molecule via an oxygen atom. In particular, this will be a tertiobutyloxy group.

The base containing an alkaline metal will in particular be selected from NaH, $NaNH_2$, potassium or lithium hexamethyldisilazane (KHMDS or LiHMDS), butyl lithium, hexyl lithium, sodium or potassium tertiobutylate or lithium diisopropylamide (LDA). Advantageously, this will be NaH or $NaNH_2$, and preferably this will be $NaNH_2$.

With the subsequent basic treatment, it is possible to hydrolyze the nitrile function of the compound (3) into a carboxylic acid in order to obtain the compound (4). An alkaline metal hydroxide is particularly suitable for this treatment, such as NaOH or KOH, and in particular NaOH.

Moreover, with the acid treatment it is possible to cyclize the hydroxyl acid derivative (4) into a lactone (II). A particularly suitable acid for this treatment is hydrochloric acid, notably in an aqueous solution, for example at 25%.

The steps (a1), (a2) and (a3) will advantageously be carried out in a same reactor, without isolating the intermediate products (3) and (4) (a method described as a one-pot method). Under these conditions, a same and single solvent will advantageously be used for these 3 steps, and preferably this will be toluene, the base and the acid of steps (a2) and (a3) being however advantageously introduced in the form of an aqueous solution.

Step (b):

By <<alkaline metal>>, is more particularly meant sodium, potassium and lithium.

$MNEt_2$ may notably be obtained by reaction of $NHEt_2$ with an alkaline metal alkoxide. $MNEt_2$ will then be advantageously formed in situ, i.e. by addition of two reagents, $NHEt_2$ and alkaline metal alkoxide, in the reaction medium containing the lactone.

By <<alkaline metal alkoxide>>, is meant in the sense of the present invention a compound of formula Alk-O-M, wherein M represents an alkaline metal as defined above and Alk represents a saturated, linear or branched hydrocarbon chain, including from 1 to 6, preferably from 1 to 4 carbon atoms. This will be in particular MeONa, MeOK, EtONa or further EtOK.

When M=Li, $LiNEt_2$ may be formed by addition of a lithium derivative, such as butyl lithium, on $NHEt_2$. In this case, $LiNEt_2$ will preferably be prepared beforehand before being introduced into the reaction medium containing the lactone.

By <<lithium derivative>>, is notably meant in the sense of the present invention, a derivative of formula Alk' Li with Alk' representing a saturated, linear or branched hydrocarbon chain, including from 1 to 6, preferably from 1 to 4 carbon atoms. This in particular is butyl lithium.

By <<Lewis acid>>, is meant in the sense of the present invention, a chemical entity capable of accepting an electron doublet and therefore capable of forming a complex with the oxygen atom of the carbonyl C=O of the lactone (II). With this, the carbonyl of the lactone may be activated and therefore the addition of the nucleophilic compound ($NHEt_2$) on the latter may be promoted. In particular, the Lewis acid may be $AlCl_3$.

Preferably, this step will be carried out in the presence of diethylamine and a complex $AlCl_3$—$NHEt_2$.

This step may notably be carried out in toluene as a solvent, including in the case of the use of $NHEt_2$ in the presence of a Lewis acid, while a Friedel-Crafts acylation reaction might have been expected between the lactone and toluene in the presence of a Lewis acid such as $AlCl_3$.

Preferably, this step will be carried out in the presence of $NHEt_2$ and $AlCl_3$ as a Lewis acid.

Step (c):

During this chlorination step, hydrochloric acid is formed. It is important to remove this compound before the next step. By using a solvent such as toluene, its removal may be facilitated by concentration of the reaction medium. Indeed, with toluene, it is possible to remove hydrochloric acid by co-evaporation more easily than with a solvent such as methylene chloride, because of its higher boiling point.

Step (d):

This step will be advantageously conducted with the potassium salt of phthalimide. The reaction may advantageously be conducted in toluene as a solvent.

Step (e):

This step of hydrolysis of the phthalimide derivative into a primary amine is advantageously carried out by reaction with hydrazine, an alkylamine such as methylamine, or a hydroxyalkylamine such as ethanolamine.

By <<alkylamine>>, is meant in the sense of the present invention, an amine of formula Alk" $NH_2$ with Alk" representing a saturated, linear or branched hydrocarbon chain, including from 1 to 6, preferably from 1 to 4 carbon atoms. In particular, this is methylamine.

By <<hydroxyalkylamine>>, is meant in the sense of the present invention, a hydroxyl-amine of formula HO—$R^2$—$NH_2$ with $R^2$ representing a saturated, linear or branched hydrocarbon chain, including from 1 to 6, preferably from 1 to 4 carbon atoms. In particular this is ethanolamine.

Preferably, this step will be carried out in the presence of ethanolamine.

This step may advantageously be carried out in a solvent such as toluene. However, hydrazine, alkylamine or hydroxyalkylamine may be added in the form of an aqueous solution.

Step (f):

With this step, it is possible to salify (1S,2R)-milnacipran obtained in the previous step (e) and at the same time to purify and isolate the acid addition salt of (1S,2R)-milnacipran by crystallization and then filtration.

Preferably, this step will be carried out in the presence of hydrochloric acid in order to form (1S,2R)-milnacipran hydrochloride.

Advantageously, the system of solvents used for the salification will comprise toluene, and preferably will be a mixture of toluene, isopropyl acetate and isopropanol.

Preferably, this mixture will have the following composition, relatively to the total volume of the solvents:

- 0 to 50%, advantageously from 30 to 40%, by volume of toluene,
- 40 to 90%, advantageously from 50 to 80%, by volume of isopropyl acetate, and
- 5 to 25%, advantageously from 10 to 20%, by volume of isopropanol.

In particular, steps (a) to (e) will advantageously be carried out in a reaction medium comprising a same and single solvent such as toluene.

Indeed, by using a same and single solvent on the whole of the steps (except for the last salification step), it is possible to simplify the procedure for preparing the compound and to reduce the cost thereof insofar that the solvent does not have to be changed at each step. Under these conditions, it is therefore not necessary to isolate the reaction intermediates even if extraction steps may be carried out in order to remove some impurities which may be bothersome for the proper progression of the following steps.

The inventors have thus discovered that the whole of the reaction sequence may unexpectedly be carried out with a same and single solvent for steps (a) to (e), and preferably with toluene.

Under these conditions, it will be advantageous to not isolate any of the intermediate products obtained in steps (a) to (d), and preferably (a) to (e), from the reaction medium. It is thus understood that the obtained intermediate products will always been in solution in the reaction medium, preferably in toluene, and will never be isolated in dry or quasi-dry form. Steps for concentrating the reaction medium may however be carried out, in particular following extraction steps, but it will be advantageous to not dry evaporate the reaction medium notably for reasons of cost and convenience. This has the additional advantage of avoiding additional product losses during intermediate purification steps.

Thus, with such a method, it is possible to obtain (1S,2R)-milnacipran with an enantiomeric excess (ee) of at least 95%, and preferably of at least 98%, and advantageously with a yield greater than 40%, preferably greater than 45%, relatively to the (R)-epichlorhydrin used as a starting product.

The object of the present invention is also the compound of following formula (IV), in the (1S,2R) enantiomeric form:

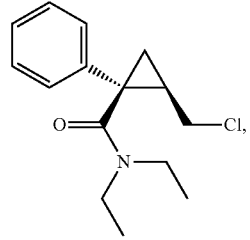

(IV)

in particular, as a synthesis intermediate.

This compound is advantageously obtained with an enantiomeric excess greater than 90%, preferably greater than 95%, and still preferably greater than 98%.

The present invention will be better understood in the light of the non-limiting examples which follow.

EXAMPLES (1S,2R)-milnacipran hydrochloride, on a basis of 41 kg of finished product is synthesized according to the following scheme and operating procedure:

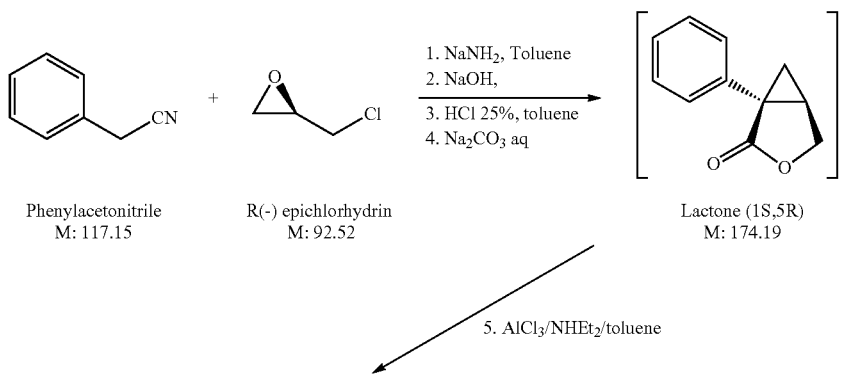

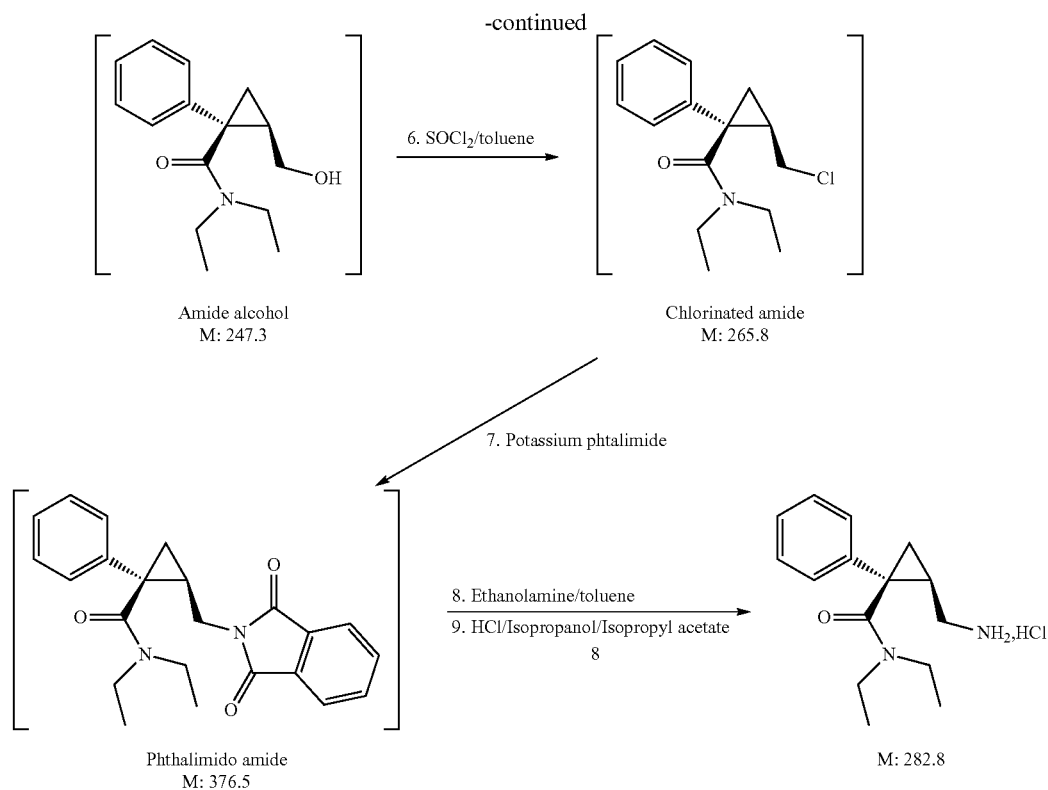

Steps 1 to 4:

28 kg of sodium amide (682 moles) are suspended in 400 L of toluene and then under intense stirring, 85.5 kg of phenylacetonitrile (729.5 moles) diluted in 10 L of toluene are poured at a temperature comprised between 0 and 5° C. The reaction medium is stirred for at least 1 hour at 10° C. 27 kg of chiral epichlorhydrin (292 moles) in solution in 20 L of toluene are added while maintaining the temperature at 10° C. At the end of the pouring, the medium is stirred for at least 2 hours. Hydrolysis is carried out by pouring the reaction medium on an aqueous solution of 240 L while maintaining the temperature between 5 and 40° C. After concentration of the obtained solution, 115 kg of 30% soda are added and the medium is heated to 95° C. in order to allow hydrolysis of the nitrile functions. The medium is washed twice with 190 L of toluene. The toluene phases are removed and the aqueous phase is recovered after adding 270 L of toluene and acidified by a 25% hydrochloric acid solution down to a pH comprised between 1 and 2. The medium is then heated to 60° C. for at least 3 hours. After decantation, the toluene phase containing the lactone is washed with 140 L of water neutralized by a 10% sodium carbonate solution up to a pH comprised between 8 and 9 and then again washed with 140 L of water. The obtained toluene phase is concentrated up to a volume of 120 L containing 38 kg of lactone (218 moles).

Step 5:

34 kg of aluminium chloride (255 moles) are suspended in 240 L of toluene and then 38.3 kg of diethylamine (523.5 moles) are added while maintaining the temperature between and 30° C. The lactone concentrate (38 kg) obtained earlier is poured on the medium maintained at 25° C. The reaction medium is stirred for at least 1 hour 30 minutes. Formation of a precipitate is observed.

This reaction medium is hydrolyzed with 345 L of water and then filtered after adding a filtration adjuvant.

After decantation, the organic phase is washed twice with 235 L and 175 L of water and then concentrated until an amide-alcohol concentrate of 110 L is obtained.

Step 6:

24.7 kg of thionyl chloride (207 moles) are poured on the concentrate within 1 hour at 25° C. under intense stirring. The reaction medium is concentrated in vacuo by limiting the temperature to 50° C. This concentration operation is repeated twice after adding twice 62 L of toluene, in order to obtain a concentrate of chlorinated amide.

Step 7:

The chlorinated amide concentrate obtained in the previous step is poured on a suspension of potassium phthalimide (51.9 kg of potassium phthalimide (280 moles) in 155 L of toluene), and the medium is heated to 85° C. for at least 3 hours. The reaction medium is cooled to 45° C., washed twice with 130 L of water. After decantation, the obtained toluene phase contains about 74 kg of phthalimido-amide (196.5 moles).

Step 8:

92.4 kg of ethanolamine (1513 moles) are introduced into the toluene solution of phthalimido-amide under intense stirring; the medium is heated to 82.5° C. for 2 hours. After cooling and adding 247 L of toluene, the reaction medium is washed with 225 L of aqueous saline 20% NaCl solution. After 2 counter-extractions of the aqueous phase with 52 L of toluene, the toluene phases are grouped and washed twice with 225 L of saline 20% NaCl solution. After decantation, 185 L of water are added on the toluene phase and the medium is acidified to a pH comprised between 2 and 3 with 25% hydrochloric acid. After decantation, the acid organic phase is again extracted with 74 L of water. The organic phase is then removed. The grouped acid aqueous phases are extracted twice with 370 and 150 L of toluene after returning to a basic pH comprised between 12 and 13 with an aqueous 20% soda solution. The grouped organic phases are washed with 80 L of water and then concentrated.

Step 9:

On the toluene concentrate, are added 283 L of isopropyl acetate and 48.4 L of isopropanol. A 5N hydrochloric acid solution in isopropanol is poured onto this organic solution, down to a pH comprised between 3 and 4 (about 30 L of solution) at a temperature of 30° C. During the introduction of the acid solution, the hydrochloride precipitates, the medium is cooled to 10° C. and maintained for at least 2 hours at this temperature. The suspension is filtered, washed 3 times with 56 L of isopropyl acetate. The obtained product is dried in vacuo at 70° C. 41 kg of (1S,2R)-milnacipran hydrochloride (145 moles) are obtained, i.e. a yield of 49.6% relative to the chiral epichlorhydrin.

The invention claimed is:

1. A method for synthesizing a pharmaceutically acceptable acid addition salt of (1S,2R)-milnacipran of the following formula (I):

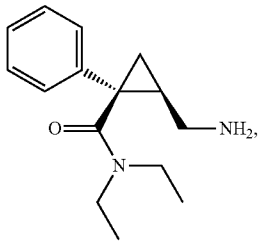

(I)

said method comprising the following successive steps:
(a) reaction of phenylacetonitrile and of (R)-epichlorhydrin in the presence of a base containing an alkaline metal, followed by a basic treatment, and then by an acid treatment in order to obtain the lactone of the following formula (II):

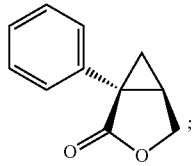

(II)

(b) reaction of the lactone (II) obtained in the previous step (a) with MNEt$_2$, wherein M represents an alkaline metal, or with NHEt$_2$ in the presence of a Lewis acid-amine complex wherein the amine is selected from diethylamine, triethylamine, diisopropylethylamine, N,N-diethylaniline, N,N-dimethylbenzylamine, N-methylpiperidine, N-methylmorpholine, N,N'-dimethylpiperazine and hexamethylene tetramine, in order to obtain the amide-alcohol of the following formula (III):

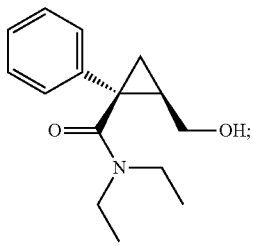

(III)

(c) reaction of the amide-alcohol of formula (III) obtained in the previous step (b) with thionyl chloride in order to obtain the chlorinated amide of the following formula (IV):

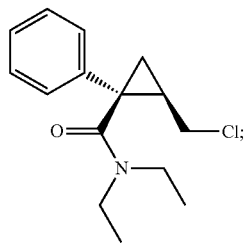

(IV)

(d) reaction of the chlorinated amide of formula (IV) obtained in the previous step (c) with a phthalimide salt, in order to obtain the phthalimide derivative of the following formula (V):

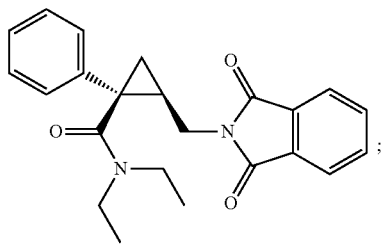

(V)

(e) hydrolysis of the phthalimide group of the phthalimide derivative of formula (V) obtained in the previous step (d), in order to obtain (1S,2R)-milnacipran; and
(f) salification of the (1S,2R)-milnacipran obtained in the previous step (e) in a suitable system of solvents, in the presence of a pharmaceutically acceptable acid,
wherein steps (a) to (e) are carried out in a reaction medium comprising a same and single toluene solvent.

2. The method according to claim 1, wherein none of the intermediate products obtained in steps (a) to (d) is isolated from the reaction medium.

3. The method according to claim 1, wherein step (b) is carried out in the presence of NHEt$_2$ and AlCl$_3$ as a Lewis acid.

4. The method according to claim 1, wherein the hydrolysis step (e) is carried out by reaction with hydrazine, an alkylamine or a hydroxyalkylamine.

5. The method according to claim 1, wherein the salification step (f) is carried out in the presence of hydrochloric acid in order to obtain (1S,2R)-milnacipran hydrochloride.

6. The method according to claim 1, wherein the salification step (f) is carried out in a system of solvents comprising toluene.

7. The method according to claim 6, wherein the system of solvents is a mixture of toluene, isopropyl acetate and isopropanol.

8. The method according to claim 7, wherein the system of solvents has the following composition, relatively to the total volume of the solvents:
0 to 50% by volume of toluene,
40 to 90% by volume of isopropyl acetate, and
5 to 25% by volume of isopropanol.

9. The method according to claim 1, wherein the phthalimide salt in step (d) is the potassium salt of phthalimide.

10. The method according to claim 2, wherein none of the intermediate products obtained in steps (a) to (e) is isolated from the reaction medium.

11. The method according to claim 4, wherein the alkylamine is methylamine and the hydroxyalkylamine is ethanolamine.

12. The method according to claim 8, wherein the system of solvents has the following composition, relatively to the total volume of the solvents:

30 to 40% by volume of toluene, 50 to 80% by volume of isopropyl acetate, and 10 to 20% by volume of isopropanol.

* * * * *

UNITED STATES PATENT AND TRADEMARK OFFICE
CERTIFICATE OF CORRECTION

PATENT NO. : 8,604,241 B2  
APPLICATION NO. : 13/146361  
DATED : December 10, 2013  
INVENTOR(S) : Marc Nicolas et al.

Page 1 of 1

It is certified that error appears in the above-identified patent and that said Letters Patent is hereby corrected as shown below:

IN THE SPECIFICATION:

At column 7, lines numbered 61-62, change "between and 30°C" to --between 15 and 30°C--.

Signed and Sealed this
Eighteenth Day of August, 2015

Michelle K. Lee
*Director of the United States Patent and Trademark Office*